(12) United States Patent
Arvinte

(10) Patent No.: US 6,436,901 B1
(45) Date of Patent: Aug. 20, 2002

(54) PHARMACEUTICAL COMPOSITIONS

(75) Inventor: Tudor Arvinte, Riehen (CH)

(73) Assignees: UCP Gen-Pharma AG, Zurich; Novartis Corporation, Basel, both of (CH)

(*) Notice: Subject to any disclaimer, the term of this patent is extended or adjusted under 35 U.S.C. 154(b) by 0 days.

(21) Appl. No.: 09/303,970

(22) Filed: May 3, 1999

Related U.S. Application Data

(63) Continuation of application No. 08/682,525, filed as application No. PCT/IB95/00053 on Jan. 25, 1995, now abandoned.

(30) Foreign Application Priority Data

Jan. 26, 1994 (GB) ............................................ 9401447

(51) Int. Cl.⁷ ......................... A61K 38/58; A01N 37/18
(52) U.S. Cl. .............................. 514/12; 514/2; 514/21; 530/324
(58) Field of Search ............................... 514/2, 12, 21; 530/324

(56) References Cited

U.S. PATENT DOCUMENTS

| | | |
|---|---|---|
| 4,668,662 A | 5/1987 | Tripier |
| 4,767,742 A | 8/1988 | Dodt et al. |
| 4,944,943 A | 7/1990 | Eschenfelder et al. ... 424/94.64 |
| 5,472,938 A | 12/1995 | Arvinte |
| 5,733,874 A | 3/1998 | Arvinte |

FOREIGN PATENT DOCUMENTS

| | | |
|---|---|---|
| EP | 0142860 | 5/1985 |
| EP | 0158564 | 10/1985 |
| EP | 0158986 | 10/1985 |
| EP | 0352227 | 1/1990 |
| EP | 0 468 327 A2 | 7/1991 |
| EP | 0503829 | 3/1992 |
| WO | WO 86/03493 | 6/1986 |

OTHER PUBLICATIONS

Degryse E. et al. "Influence of Storage Conditions on the Activity of Recombinant Hirudin". Thrombosis Research, vol. 61, 1991, New York, pp. 87–89.

Johnson et al. "Biochemistry and Genetic Engineering of Hirudin". Seminars in Thrombosis and Hemostasis. vol. 15, No. 3 (1989) New York, pp. 302–315.

Longstaff et al. "An International Collabative Study to Investigate Standardisation of Hirudin Potency". Thrombosis and Haemostasis, vol. 69, No. 5, 1993 Stuttgart, pp. 430–435.

European Search Report.

Primary Examiner—Geetha P. Bansal
(74) Attorney, Agent, or Firm—Hesna J. Pfeiffer

(57) ABSTRACT

The present invention provides a freeze dried pharmaceutical composition comprising hirudin, potassium phosphate and a sugar.

3 Claims, 1 Drawing Sheet

PHARMACEUTICAL COMPOSITIONS

Figure 1:
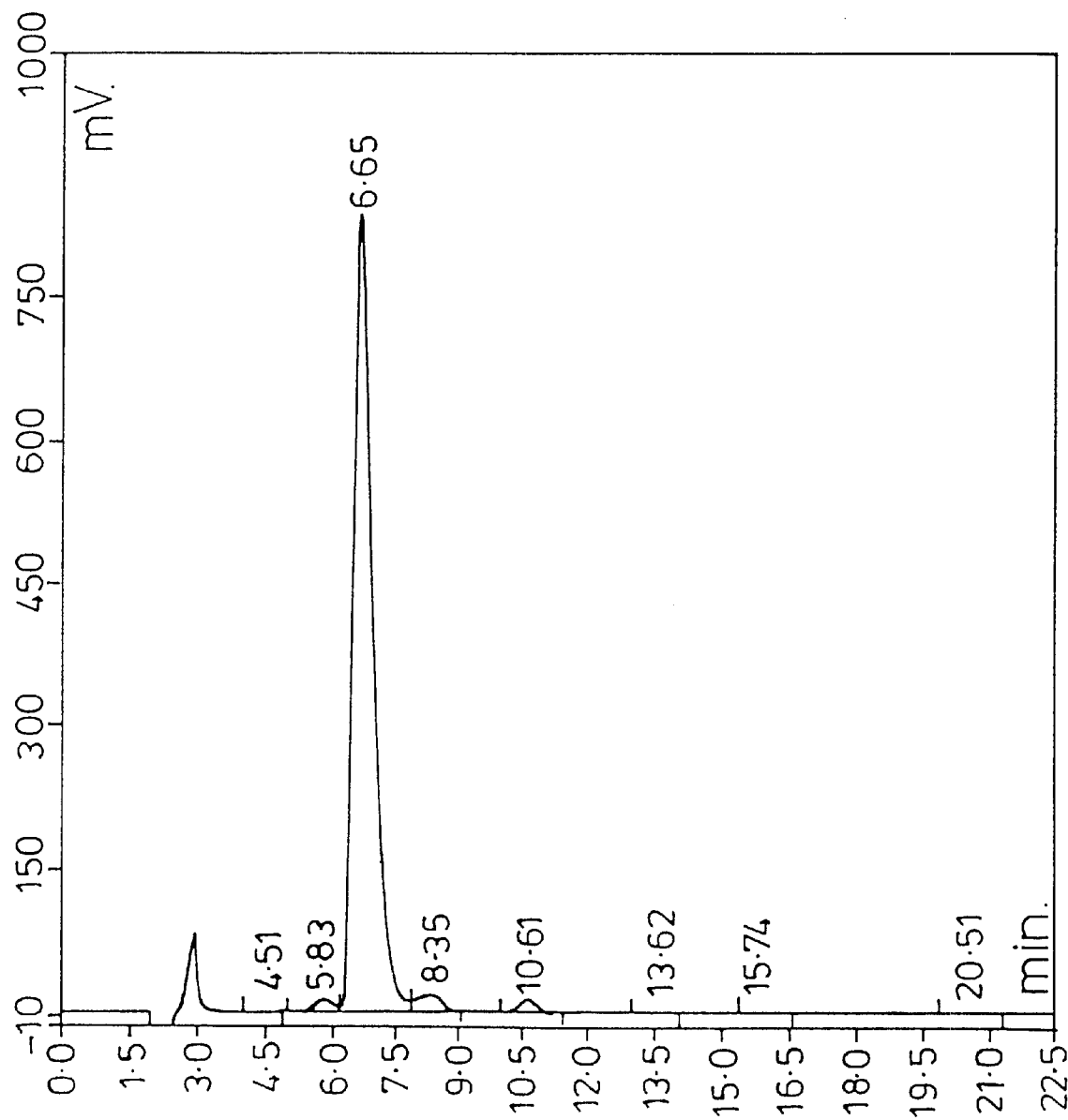

This application is a continuation of Ser. No. 08/682,525 filed Jan. 23, 1997, abandoned, which is the U.S. national stage of PCT/IB95/00053, filed Jan. 25, 1995.

The present invention relates to compositions containing hirudin and in particular to stable powder formulations.

Hirudin, an anticoagulant naturally occurring in leeches (*Hirudo medicinalis*), is not a single polypeptide species but a class of equally acting polypeptides consisting of at least four representatives designated hirudin variant 1 (HV1), hirudin variant 2 (HV2) (cf. European Patent Application No. 158 564) hirudin variant 3 (PA) [cf. PCT-Application No. 86/03493] and "des-(Val)$_2$-hirudin" (cf. European Patent Application No. 158 986). The variants differ in structure from each other by a number of amino acids (especially, the N-terminal sequence of HV1 is Val-Val-Tyr, that of HV2 and of HV3 is Ile-Thr-Tyr and that of "des-(Val)$_2$-hirudin" is Thr-Tyr) but have an accumulation of hydrophobic amino acids at the N-terminus and of polar amino acids at the C-terminus, a tyrosine residue (Tyr$^{63}$) present as sulphate monoester, three disulphide bridges and the anticoagulant activity in common.

In the past few years cDNAs and synthetic genes coding for hirudin variants have been cloned and expressed in microbial hosts. Although the expression products lack the sulphate monoester group at Tyr$^{63}$- and were therefore designated "desulphatohirudins"—they turned out to exhibit approximately the same biological activity as the natural, sulphated hirudins. Desulphatohirudin variant HV1 has been expressed in *Escherichia coli* (European Patent Applications No. 158 564 and 168 342) and in *Saccharomyces cerevisiae* (European Patent Applications No. 168 342, 200 655, 225 633, 252 854 and 341 215). Similarly, desulphatohirudin HV2 has been expressed in *Escherichia coli* (European Patent Applications No. 158 564) and in *Saccharomyces cerevisiae* (European Patent Application No. 200 655, PCT-Application No. 86/01224] and des-(Val)$_2$-desulphatohirudin has been expressed in *Escherichia coli* (European Patent Application No. 158 986).

According to the present invention, the term "hirudin" is intended to embrace hirudin, desulphathohirudin, a hirudin variant or a desulphatohirudin variant or a mutant thereof, respectively, described in the literature and in particular a desulphatohirudin compound or a mutant thereof obtainable from a transformed microorganism strain containing DNA which codes for a desulphatohirudin or a mutant thereof. Such desulphatohirudins are, for example, desulphatohirudin variant HV1, HV1 modified (a, b), HV2, HV2 modified (a, b, c), HV3, variants of HV3 and des (Val$_2$)-desulphatohirudin.

Preferred desulphatohirudins are those having the formula (SEQ ID NO: 1)

```
Val Val Tyr Thr Asp Cys Thr Glu Ser Gly Gln Asn Leu Cys Leu Cys   (I)
 1               5                   10                  15

Glu Gly Ser Asn Val Cys Gly Gln Gly Asn Xaa Cys Ile Leu Gly Ser
             20                  25                  30

Asp Gly Glu Xaa Asn Gln Cys Val Thr Gly Glu Gly Thr Pro Xaa Pro
             35                  40                  45

Gln Ser Xaa Asn Asp Gly Asp Phe Glu Glu Ile Pro Glu Xaa
             50                  55                  60
``` in which
a) Xaa at 27, 36 end 47 are each Lys, Xaa at 51 is His and Xaa at 62 is the peptide residue Glu-Tyr-Leu-Gln (HV1), or
b) Xaa at 27 is Ile or Glu and Xaa at 36,47,51 and 62 are as defined in a) (HV1 modified a), or
c) Xaa at 36 is Ile or Glu and Xaa at 27, 47, 51 and 62 are as defined in a) (HV1 modified a), or
d) Xaa at 47 is Ile or Glu and Xaa at 27, 36, 51 and 62 are as defined in a) (HV1 modified a), or
e) Xaa at 51 is Leu or Asp and Xaa at 27, 36, 47 and 62 are as defined in a) (HV1 modified a), or
f) Xaa at 62 is selected from the group consisting of Glu-Tyr, Glu-Tyr-Leu, Glu-Asp-Leu-Gln, Glu-Glu-Leu-Gln, Glu-Tyr-Lys-Arg, Glu-Asp-Lys-Arg, Glu-Lys-Leu-Gln, Ser-Phe-Arg-Tyr, Trp-Glu-Leu-Arg, Glu-Tyr-Leu-Gln-Pro and Glu-Tyr-Leu-Gln-Arg and Xaa at 27, 36, 47 and 51 are as defined in a) (HV1 modified b),
or having the formula (SEQ ID NO: 2)

```
Leu Thr Tyr Thr Asp Cys Thr Glu Ser Gly Gln Asn Leu Cys Leu Cys   (II)
 1               5                   10                  15

Glu Gly Ser Asn Val Cys Gly Gln Gly Asn Lys Cys Ile Leu Gly Ser
             20                  25                  30

Asp Gly Glu Lys Asn Gln Cys Val Thr Gly Glu Gly Thr Pro Lys Pro
             35                  40                  45

Gln Ser His Asn Asp Gly Asp Phe Glu Glu Ile Pro Glu Glu Tyr Leu
             50                  55                  60
```

-continued

Gln
65 or having the formula (SEQ ID NO: 3)

```
Ile Thr Tyr Thr Asp Cys Thr Glu Ser Gly Gln Asn Leu Cys Leu Cys   (III)
1             5                         10                   15

Glu Gly Ser Asn Val Cys Gly Lys Gly Asn Lys Cys Ile Leu Gly Ser
            20                  25                  30

Asn Gly Lys Gly Asn Gln Cys Val Thr Gly Glu Gly Thr Pro Xaa Pro
        35                  40                  45

Glu Ser His Asn Asn Gly Asp Phe Glu Glu Ile Pro Glu Glu Xaa Leu
        50                  55                  60

Gln
65
``` in which
a) Xaa at 47 is Asn and Xaa at 63 is Tyr (HV2), or
b) Xaa at 47 is Lys, Arg or His and Xaa at 63 is Tyr (HV2 modified a), or
c) Xaa at 63 is Glu or Asp and Xaa at 47 is Asn (HV2 modified b), or having the formula SEQ ID NO: 4)

```
Val Val Tyr Thr Asp Cys Thr Glu Ser Gly Gln Asn Leu Cys Leu Cys   (IV)
1             5                         10                   15

Glu Gly Ser Asn Val Cys Gly Lys Gly Asn Lys Cys Ile Leu Gly Ser
            20                  25                  30

Asn Gly Lys Gly Asn Gln Cys Val Thr Gly Glu Gly Thr Pro Asn Pro
        35                  40                  45

Glu Ser His Asn Asn Gly Asp Phe Glu Glu Ile Pro Glu Glu Tyr Leu
        50                  55                  60

Gln
65
``` or having the formula (SEQ ID NO: 5)

```
Ile Thr Tyr Thr Asp Cys Thr Glu Ser Gly Gln Asn Leu Cys Leu Cys   (V)
1             5                   10                   15

Glu Gly Ser Asn Val Cys Gly Lys Gly Asn Lys Cys Ile Leu Gly Ser
            20                  25                  30

Gln Gly Lys Asp Asn Gln Cys Val Thr Gly Glu Gly Thr Pro Lys Pro
        35                  40                  45

Gln Ser His Asn Gln Gly Asp Phe Glu Pro Ile Pro Glu Asp Ala Tyr
        50                  55                  60

Asp Glu
65
```

HV3 and variants of said HV3 which are characterised by a shortening of the primary structure by 1 or 2 amino acids at the N-terminus or by 18, 10, 9, 6, 4 or 2 amino acids at the C-terminus.

Particularly preferred desulphatohirudin compounds are those of formula I in which the Xaa groups are as defined under a) or the compound of formula III in which Xaa at 47 is Lys and Xaa at 63 is Tyr.

The most preferred hirudin is desulfatohirudin HV1 having the formula I in which Xaa at 27, 36 and 47 are each Lys, Xaa at 51 is His and Xaa at 62 is the peptide residue Glu-Tyr-Leu-Gln.

The hirudins used in the present invention can be prepared synthetically, e.g. chemically or preferably by recombinant techniques, or by isolation from leeches.

According to the present invention the term "mutant" refers to proteins (muteins) exhibiting antithrombotic activity which differ from native hirudin or desulphathohirudin by simple or multiple mutations (cf. European Patent Applications No. 352 227 and No. 352 228). The DNA coding for said mutants which can be prepared by methods known in the art e.g. site-directed mutagensis, is cloned and expressed in microbial hosts such as *Escherichia coli* and *Saccharomyces cerevisiae*.

The hirudin compounds used in the invention can be in the free form but also in the form of their salts. As they contain free amino group in several amino acid residues, the compounds can be in the form of acid addition salts. Suitable acid addition salts are in particular pharmacologically acceptable salts with conventional therapeutically acceptable acids. Representative inorganic acids are hydrohalic acids (such as hydrochloric acid), and also sulfuric acid, phosphoric acid and pyrophosphoric acid. Representative organic acids are in particular arenesulfonic acids (such as benzenesulfonic or p-toluenesulfonic acid), or lower alkanesulfonic acids (such as methanesulfonic acid), as well as carboxylic acids such as acetic acid, lactic acid, palmitic acid, stearic acid, malic acid, tartaric acid, ascorbic acid and citric acid. As, however, the compound used in the invention also contains free carboxyl groups in several amino acid residues, which carboxyl groups impart acidic character to the entire peptide, they can also be in the form of salts with inorganic or organic bases, e.g. sodium, potassium, calcium or magnesium salts, or also ammonium salts derived from ammonia or a pharmacologically acceptable organic nitrogen-containing base. However, as they contain at the same time free carboxyl groups and free amino groups, they can also be in the form of inner salts. Pharmacologically acceptable salts are preferred.

One problem in developing a dosage form containing hirudin is its poor stability in aqueous solutions and in powder form.

The poor stability can be seen when hirudin is analysed by chromatographic methods, such as reverse phase HPLC (RP-HPLC).

RP-HPLC method: A LiChroCART 125-4 column is used (Merck LiChrospher 100 RP-18 5 μm). Solvent A is 0.5% ammoniumacetate in acetonitrile/water (10:90), (v:v); solvent B is 0.5% ammoniumacetate in acetonitrile/water (25:75). The elution is performed at 45° C. using a flow rate of 0.5 ml/min. The binary elution is a linear gradient starting at time zero with 23% solvent B and reaching 46% solvent B after 24 minutes. After 2 min at 70% solvent B the column is equilibrated for 7 min at 23% solvent B.

A typical chromatogram of recombinant hirudin HV1 (CGP 39393) in water using the RP-HPLC (1 mg/ml hirudin) method is shown in FIG. 1.

In FIG. 1 the relative area of the main peak is 95.15%. Storage of hirudin in water at room temperature results in an increase of by products with time. This shows itself by a decrease in the area of the main peak and an increase in the area of the small peaks. The changes which occur can be accelerated by using temperature stress experiments i.e. by storage at elevated temperatures.

We have now found that potassium phosphate can be used to increase the stability of hirudin.

Accordingly the present invention provides a freeze dried pharmaceutical composition comprising hirudin, potassium phosphate and a sugar.

The composition of the invention may be produced by forming an aqueous solution of the ingredients and then freeze drying it in a conventional manner.

The potassium phosphate is preferably dipotassium hydrogen phosphate. It may be used, in the solution before freeze drying, at a molarity of from 0.1 to 0.5, preferably from 0.1 to 0.3.

Suitable sugars include mannitol, trehalose, sucrose, sorbitol, fructose, glucose, maltose, lactose and dextran. The preferred sugars are mannitol and trehalose.

The amount of sugar in the solution before freeze drying may be such as to produce a concentration of from 5 to 50% (w/v) and preferably from 5 to 20% (w/v). The solution before freeze drying is preferably isotonic.

The pH of the solution before freeze drying may be from 4 to 10, preferably from 6 to 9 and most preferably from 6.5 to 8.

If desired a citrate buffer may be added to the solution before freeze drying e.g. by adding citric acid. The molarity of the citrate may be from 0.1 to 0.5, preferably from 0.1 to 0.3.

The concentration of hirudin in the solution before freeze drying may be from 0.1 to 500 mg/ml, preferably from 20 to 250 mg/ml.

The freeze dried product is stable for long periods of time without the need for refrigerated storage. In addition, after the product has been redissolved in water, the resulting solution is also stable for long periods although the stability in solution is not as good as the stability of the freeze dried powder.

The solutions made by redissolving the freeze dried product may be used in the production of standard ampoules, pre-filled double camber syringes, or multi-administration systems. The solutions may of course also be used immediately for administration.

The invention is illustrated by the following Examples.

EXAMPLE 1

Aqueous solutions of recombinant desulphatohirudin HV1 (CGP 39393 from Ciba-Geigy) are produced by dissolving it (a) water; (b) 70 parts by volume of a 5% trehalose solution and 30 parts by volume of a citric acid/$K_2HPO_4$ mixture, 150 mM at pH 7.4; (c) 30 parts by volume of a 5% mannitol solution and 70 parts by volume of a citric acid/$K_2HPO_4$ mixture, 150 mM at pH 7.4; and (d) 30 parts by volume of a 5% mannitol solution and 70 parts by weight $K_2HPO_4$, 150 mM at pH 7.4. In each case the concentration of hirudin is 30 mg/ml.

The solutions are freeze dried and stored at 46° C. At different times, samples are dissolved in water to 1 mg/ml hirudin and the main peak measured by RP-HPLC. The results obtained are given in Table 1 below.

TABLE 1

| | % main peak area after | | | | |
|---|---|---|---|---|---|
| System | 11 days | 42 days | 103 days | 132 days | 162 days |
| (a) | 85.1 | 80.4 | 71.9 | 65.5 | 61.0 |
| (b) | 92.6 | 93.2 | 90.8 | 86.9 | 89.7 |
| (c) | 93.9 | 90.8 | 85.0 | 83.1 | 83.6 |
| (d) | 92.4 | 90.5 | 85.5 | 83.5 | 84.0 |

It can be seen that the stability is maintained at a high level even when stored for extended periods at 46° C.

EXAMPLE 2

Aqueous solutions of recombinant desulphatohirudin HV1 (CGP 39393 from Ciba-Geigy) are made by dissolving it in different sugar/citrate/phosphate mixtures as follows. In each case 30 parts by volume sugar is mixed with 70 parts by volume citrate/phosphate.

man 5%: CKP—100 mM $K_2HPO_4$ (1.74%); 7 mM citric acid (0.134%); 82 mM mannitol(1.5%); 4 mM hirudin (0.3%).

suc 10%: CKP—100 mM $K_2HPO_4$ (1.74%); 7 mM citric acid (0.134%); 87.6 mM sucrose (3%); 4 mM hirudin (0.3%).

tre 10%: CKP—100 mM $K_2HPO_4$ (1.74%); 7 mM citric acid(0.134%); 87.6 mM trehalose (3%); 4 mM hirudin (0.3%).

The solutions are freeze dried and stored at different temperatures. After a certain storage time a sample is redissolved in water to 1 mg/ml hirudin and the main peak measured by RP-HPLC. The results obtained are given in Table 2 below.

TABLE 2

| | % main peak area after | | | |
|---|---|---|---|---|
| System | 8 days 79° C. | 55 days 59° C. | 55 days 46° C. | 132 days 26° C. |
| Water | 34.0 | 59.6 | 75.9 | 89.6 |
| man 1.5%: CKP | 67.0 | 82.2 | 91.0 | 94.6 |
| suc 3%: CKP | 76.1 | 86.8 | 91.5 | 94.4 |
| tre 3%: CKP | 80.2 | 87.0 | 91.3 | 94.3 |

The improved stability can be seen when the powder is stored at various temperatures. At 26° C. which is probably slightly higher than normal ambient conditions there is no degradation noticeable after 132 days.

What is claimed is:

1. A composition comprising hirudin, potassium phosphate, and a sugar, said composition being prepared by first forming an isotonic solution of hirudin, dipotassium hydrogen phosphate, and a sugar selected from the group consisting of mannitol, trehalose, sucrose, sorbitol, fructose, glucose, maltose, lactose, and dextran, at a concentration of hirudin of 0.1 to 500 mg/ml, and then freeze drying the solution.

2. A composition as claimed in claim 1 in which the hirudin is a desulphatohirudin HV1.

3. A composition as claimed in claim 1 which also contains a citrate.

* * * * *

SEQUENCE LISTING

```
<160> NUMBER OF SEQ ID NOS: 5

<210> SEQ ID NO 1
<211> LENGTH: 62
<212> TYPE: PRT
<213> ORGANISM: Artificial Sequence
<220> FEATURE:
<223> OTHER INFORMATION: desulphatohirudins
<221> NAME/KEY: VARIANT
<222> LOCATION: (1)...(62)
<223> OTHER INFORMATION: Xaa = Any Amino Acid

<400> SEQUENCE: 1

Val Val Tyr Thr Asp Cys Thr Glu Ser Gly Gln Asn Leu Cys Leu Cys
 1               5                  10                  15

Glu Gly Ser Asn Val Cys Gly Gln Gly Asn Xaa Cys Ile Leu Gly Ser
                20                  25                  30

Asp Gly Glu Xaa Asn Gln Cys Val Thr Gly Glu Gly Thr Pro Xaa Pro
            35                  40                  45

Gln Ser Xaa Asn Asp Gly Asp Phe Glu Glu Ile Pro Glu Xaa
        50                  55                  60

<210> SEQ ID NO 2
<211> LENGTH: 65
<212> TYPE: PRT
<213> ORGANISM: Artificial Sequence
<220> FEATURE:
<223> OTHER INFORMATION: desulphatohirudins

<400> SEQUENCE: 2

Leu Thr Tyr Thr Asp Cys Thr Glu Ser Gly Gln Asn Leu Cys Leu Cys
 1               5                  10                  15

Glu Gly Ser Asn Val Cys Gly Gln Gly Asn Lys Cys Ile Leu Gly Ser
                20                  25                  30

Asp Gly Glu Lys Asn Gln Cys Val Thr Gly Glu Gly Thr Pro Lys Pro
            35                  40                  45

Gln Ser His Asn Asp Gly Asp Phe Glu Glu Ile Pro Glu Glu Tyr Leu
        50                  55                  60

Gln
65
```

<210> SEQ ID NO 3
<211> LENGTH: 65
<212> TYPE: PRT
<213> ORGANISM: Artificial Sequence
<220> FEATURE:
<223> OTHER INFORMATION: desulphatohirudins
<221> NAME/KEY: VARIANT
<222> LOCATION: (1)...(65)
<223> OTHER INFORMATION: Xaa = Any Amino Acid
<221> NAME/KEY: VARIANT
<222> LOCATION: (1)...(65)
<223> OTHER INFORMATION: Xaa = Any Amino Acid

<400> SEQUENCE: 3

Ile Thr Tyr Thr Asp Cys Thr Glu Ser Gly Gln Asn Leu Cys Leu Cys
 1               5                  10                  15

Glu Gly Ser Asn Val Cys Gly Lys Gly Asn Lys Cys Ile Leu Gly Ser
            20                  25                  30

Asn Gly Lys Gly Asn Gln Cys Val Thr Gly Glu Gly Thr Pro Xaa Pro
        35                  40                  45

Glu Ser His Asn Asn Gly Asp Phe Glu Glu Ile Pro Glu Glu Xaa Leu
    50                  55                  60

Gln
65

<210> SEQ ID NO 4
<211> LENGTH: 65
<212> TYPE: PRT
<213> ORGANISM: Artificial Sequence
<220> FEATURE:
<223> OTHER INFORMATION: desulphatohirudins

<400> SEQUENCE: 4

Val Val Tyr Thr Asp Cys Thr Glu Ser Gly Gln Asn Leu Cys Leu Cys
 1               5                  10                  15

Glu Gly Ser Asn Val Cys Gly Lys Gly Asn Lys Cys Ile Leu Gly Ser
            20                  25                  30

Asn Gly Lys Gly Asn Gln Cys Val Thr Gly Glu Gly Thr Pro Asn Pro
        35                  40                  45

Glu Ser His Asn Asn Gly Asp Phe Glu Glu Ile Pro Glu Glu Tyr Leu
    50                  55                  60

Gln
65

<210> SEQ ID NO 5
<211> LENGTH: 66
<212> TYPE: PRT
<213> ORGANISM: Artificial Sequence
<220> FEATURE:
<223> OTHER INFORMATION: desulphatohirudins

<400> SEQUENCE: 5

Ile Thr Tyr Thr Asp Cys Thr Glu Ser Gly Gln Asn Leu Cys Leu Cys
 1               5                  10                  15

Glu Gly Ser Asn Val Cys Gly Lys Gly Asn Lys Cys Ile Leu Gly Ser
            20                  25                  30

-continued

```
Gln Gly Lys Asp Asn Gln Cys Val Thr Gly Glu Gly Thr Pro Lys Pro
        35                  40                  45

Gln Ser His Asn Gln Gly Asp Phe Glu Pro Ile Pro Glu Asp Ala Tyr
    50                  55                  60

Asp Glu
65
```